United States Patent
Thastrup et al.

[11] Patent Number: 5,721,135
[45] Date of Patent: Feb. 24, 1998

[54] APPARATUS FOR IDENTIFYING BIOLOGICALLY ACTIVE SUBSTANCES BY THEIR EFFECT ON LIVING CELLS

[75] Inventors: Ole Thastrup, Birkeroed; Kurt Scudder, Virum, both of Denmark; Jaromir Ruzicka, Seattle, Wash.

[73] Assignee: Novo Nordisk A/S, Bagsvaerd, Denmark

[21] Appl. No.: 498,735

[22] Filed: Jul. 6, 1995

[51] Int. Cl.$^6$ .................................. C12M 1/34
[52] U.S. Cl. .................. 435/286.5; 435/288.3; 435/288.7; 435/299.1; 435/305.1
[58] Field of Search ............... 435/286.5, 287.1, 435/287.9, 288.3, 288.7, 299.1, 305.1, 305.4; 359/398; 250/576

[56] References Cited

U.S. PATENT DOCUMENTS

| | | | |
|---|---|---|---|
| 4,734,372 | 3/1988 | Rotman | 435/288.7 |
| 5,312,731 | 5/1994 | Engstrom | 435/288.7 |
| 5,468,605 | 11/1995 | Harris et al. | 435/286.5 |

FOREIGN PATENT DOCUMENTS

| | | | |
|---|---|---|---|
| 514017 | 5/1976 | U.S.S.R. | 435/288.3 |
| 544676 | 1/1977 | U.S.S.R. | 435/299.1 |
| 1124021 | 11/1984 | U.S.S.R. | 435/288.3 |
| 1462192 | 2/1989 | U.S.S.R. | 435/288.2 |

*Primary Examiner*—William H. Beisner
*Attorney, Agent, or Firm*—Steve T. Zelson, Esq.; Elias J. Lambiris, Esq.

[57] ABSTRACT

The present invention relates to a rapid automated device for identifying biologically active substances by their effect on living cells which includes a flow chamber defined by a bottom wall with a plane optical surface through which the content of the chamber can be monitored and a ring shaped wall having an edge adjacent the plane optical surface leaving a gap between the edge and optical surface wherein the width of the gap allows liquid but not matrix to pass. The flow chamber also including an inlet through which fluids can be transported into the chamber and a device to control the distance between the edge and the optical surface wherein the matrix is momentarily allowed to pass.

2 Claims, 3 Drawing Sheets

APPARATUS FOR IDENTIFYING BIOLOGICALLY ACTIVE SUBSTANCES BY THEIR EFFECT ON LIVING CELLS

BACKGROUND OF THE INVENTION

1. Field of the Invention

The invention relates to the technique of identifying biologically active substances and to be more specific to identification by the effect of the substance on living cells. These biologically active compounds include, but are not limited to, drugs, insecticides, pesticides, and herbicides.

2. Description of Related Art

The practice of screening large libraries of samples of unknown composition for the few which may contain a compound of specific biological activity is one of the more common methods of new drug discovery. The samples of unknown composition are in most cases biological material, such as plant extracts or microbial fermentation broths. Screening these for biological activity is normally accomplished by performing binding assays or, more recently, functional assays.

Binding Assays. A binding assay is an attempt to find compounds of interest by identifying those which adhere with a minimum degree of affinity to cells or cell products. This can be done using fluorescent, luminescent, or radioactive detection methods. These assays are based not on a biological response, but a passive process which results from biological activity, namely the generation of specific molecules by biological systems. They cannot be construed as functional assays or as real-time assays.

Gene Expression Assays. Another way to determine biological activity is to measure up-regulation or down-regulation of expression of a known gene. This is done by inserting DNA which codes for something which can be readily measured into a cell's genome such that the expression of interest is coupled to expression of the inserted DNA. While this is a true functional assay, it also is not a real time assay. In addition, it is only capable of finding compounds which affect gene expression. In many cases this is not the response of interest.

Other Functional Assays. The CytoSensor described in U.S. Pat. No. 4,915,812 and U.S. Pat. No. 5,395,503 is a commercial instrument which has been billed as a screening instrument. It is based on the detection of increased cellular proton flux by means of a semiconducting electrode. The instrument is applicable to high through-put screening, but can only detect cellular events that result in changes in extracellular pH. Again, many responses of interest are not associated with changes in extracellular pH.

The growth over the last few decades in the knowledge of cellular signalling has presented extremely rich opportunities for new ways of screening for biologically active compounds. Armed with knowledge of the biological process which one wants to affect with a new product, it is conceivable to monitor the actual process as a way of looking for compounds which affect it. The development of fluorescent probe molecules which upon interaction with intracellular signalling molecules (e.g. ions, enzymes, cyclic nucleotides) change their spectral properties has enabled the real-time monitoring of dynamic biological responses within living cells. Most of these probes can be introduced non-invasively into cells and will, depending on the detection system, allow characterization of cellular events in high temporal resolution (microseconds to seconds) and high spatial resolution (nanometers to micrometers). This probe technology, in combination with the technology of cellular imaging which is described below, has had a major impact on cell biology in that it has enabled monitoring of complex, cross-reacting intracellular events that could not be unravelled by conventional invasive biochemical techniques.

Imaging of cellular functions using luminescent probes. Visualization of intracellular function using luminescent (fluorescent or bioluminescent) probes has become one of the mainstay techniques in modern cell biology. Using traditional optical microscopes with quantitative detectors in place of the human eye, both the concentration and distribution in the cell of a variety of intracellular molecules of interest can be measured. While luminescent probes can be measured in large populations of cells using other techniques, imaging is the only way to learn what is going on in single cells or small populations of cells. It also has the advantage of much higher optical efficiency when compared with traditional spectrophotometric techniques for measuring optical signals.

To obtain high spatial resolution it is necessary to image the cells of interest through a research grade microscope. This technique is very labor-intensive and time-consuming. Therefore, it does not lend itself to high sample volume measurements such as are necessary in high through-put screening for novel biologically active substances (e.g. drugs, insecticides, pesticides, herbicides). In these studies it is necessary to screen thousands of samples containing complex mixtures of compounds within a very short time frame. It is important that the biological activity of the samples are well characterized because if biological activity is found in a given sample, a cumbersome compound isolation and structure elucidation follows.

It is the object of the invention to provide a method by which the few biologically active samples in a large library of samples may identified in rapid succession by monitoring the effect of each sample on living cells. These cells are ones which have been specifically chosen to exhibit the desired biological behavior. They may be primary cells cultured from fresh tissue, or they may be genetically engineered cells transfected with one or more genes of interest.

SUMMARY OF THE INVENTION

The present invention relates to a method which comprises the steps of a) culturing cells on/within a matrix that can be fluidically controlled;

b) loading the cells with luminescent chemical molecules;

c) injecting a well defined volume of the cell carrying matrix suspension into a flow fluid which transports the suspension into a flow chamber having a wall through which the content of said flow chamber may be monitored;

d) exposing the cells to a sample containing the potentially biologically active substance;

e) measuring the luminescence response of the content in the flow chamber; and f) flushing the flow chamber to make it ready for a new test cycle.

BRIEF DESCRIPTION OF THE DRAWINGS

In the following the invention will be further described with references to the drawings, wherein.

DETAILED DESCRIPTION OF THE INVENTION

Figure 1:
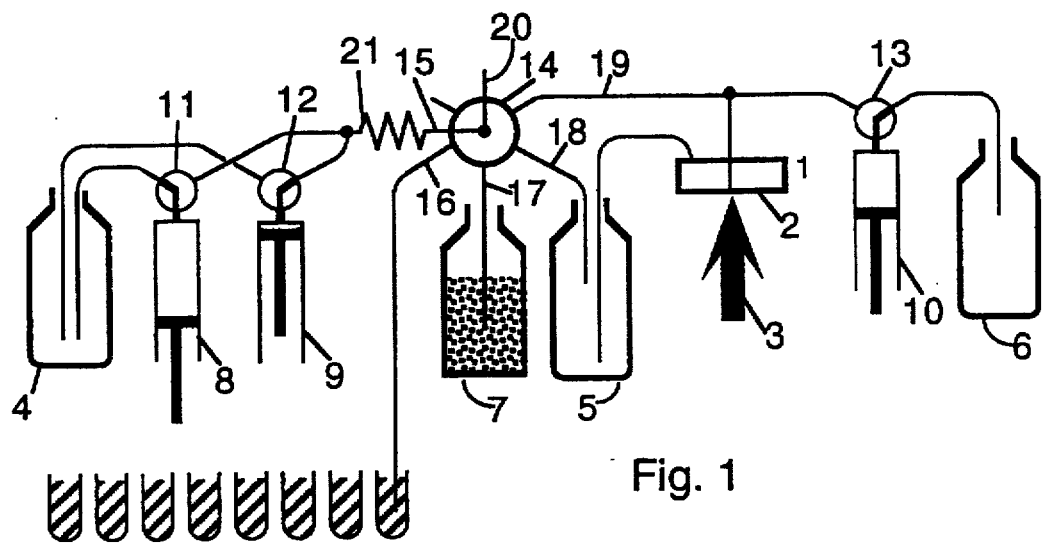
FIGS. 1–6 show schematically a diagram of the fluidic system of an apparatus in six successive step positions during the sequence run through when carrying out the method according to the invention.

The method according to the invention allows monitoring of dynamic cellular responses in living cells, while the cells are attached to a matrix (e.g. microcarrier beads) that can be fluidically controlled. Under continuous flow operation it is possible to obtain very short sample exposure times which make the invention suited to high through-put screening for novel biologically active substances. The method will also find application in the search for rare biological events associated with expression of specific proteins in transfected cell lines.

According to the invention the matrix may be provided as microcarrier beads or as microdroplets of agarose.

The method employs detection of cellular signals from cells cultured on the surface of microcarrier beads or encapsulated in microdroplets of agarose gel, the beads/droplets not only providing the support for the cells but also the vehicle for transportation of said cells from tissue culture facilities (incubators) to detection system. The flow chamber is capable of positioning the carriers in a fixed position without the aid of a human operator, and simultaneously allowing visualization through a microscope equipped with a high numerical aperture objective lens.

According to the invention the flushing of the flow chamber may advantageously be a forward flushing. By a forward flushing is meant that the flush liquid passes the chamber in the same direction as do the injected matrix carrying flow fluid. Hereby a more effective flushing is obtained as the flushing fluid simply displaces the matrix out of the chamber instead of sucking it out.

The present invention also relates to an apparatus for use in the method according to the invention.

Such an apparatus is characterized in that it comprises a flow chamber having a wall through which the content of said chamber may be monitored, a fluidic handling system for controlled sequential injection of buffer, cell carrying matrix and sample or samples into the flow chamber and for final removing of waste during a flushing of this chamber.

The flow chamber of the apparatus may comprise a plane optical surface as a wall through which the content of the chamber may be monitored, a ring shaped wall having an edge adjacent to the plane optical surface leaving a gap between said edge and said optical surface which gap allow liquid but not the matrix to pass. When a volume of buffer carrying the matrix beads or droplets is injected into the flow chamber the beads or droplets will be retained on the optical surface whereas the buffer may escape through the gap between this surface and the edge of the ring shaped wall.

Injected sample will trickle between the beads or the droplets in close contact with these beads and droplets and escape through the gap. The chamber may be flushed by sucking flushing buffer in through the gap and removing it via the inlet of the chamber until all beads and droplets are flushed away.

A quicker flushing may be obtained when the distance between the edge of the ring shaped wall and the plane optical surface may be controlled so that it momentarily allows the matrix beads or microdroplets to pass. This way the flow through the chamber may be made unidirectional and all supplies may be made to the inlet of the chamber and all draining of waste may take place from an area surrounding the inlet. This offers two advantages. First, it increases the rate at which samples may be processed by eliminating a wash step after the beads or droplets are removed. Second, it eliminates any contamination of the chamber by anything which may remain in the waste, which would ordinarily be sucked in during the flush step and have to be washed out.

Further, the width of the gap may be changed by electromagnetic means which are controlled to momentarily pull the ring shaped wall and the plane surface away from each other. This makes it easy to control the width of the gap so that it is enlarged during the flushing step of the identification cycle.

An apparatus for carrying out the identification cycle comprises as shown in FIGS. 1–6 a flow chamber 1 into which a charge of matrix beads carrying the living cells chosen for the identification is transported and exposed to the sample the influence of which shall be identified. The content of the flow chamber may be observed through a wall 2 of this chamber.

The optical portion used for the observation is illustrated by the arrow 3. This optical portion may be a standard microscope equipped for epi-illumination. The light source may be a rapid scanning monochromator which allows switching among selected wavelengths of light for excitation of the fluorescent molecules in the cells in a time scale appropriate for the response being measured. The fluorescence detector may be a photomultiplier, camera, image detector or other with sufficiently fast response to allow the signal to be detected without undersampling of the process. Both the light source and the detector are computer controlled for synchronizing the acquisition of the fluorescence signals with the appropriate excitation wavelength.

The fluidic part of the apparatus further comprises a container 4 for a buffer fluid, waste containers 5 and 6 and a container 7 for matrix beads or droplets carrying the living cells.

Further the fluidic part of the apparatus comprises three syringes 8, 9, and 10 which under computer control are sequentially operated to act as pumps providing the driving force which sends liquid through the apparatus in a way which is further controlled by two-way valves 11, 12, and 13 at the outlet ends of the respective syringes and a multi-way selection valve 14. All valves are controlled by the computer to establish the appropriate connection during the different steps of the process.

The selection valve has a main lead 15 which by the different positions of this valve may be connected to one of a number of other leads 16, 17, 18, 19 and 20. The choice of connection is controlled by the computer.

FIG. 1 shows the first step during which the syringe 8 is loaded with buffer from the container 4 whereas the syringe 9 is empty, i.e. with its piston in its innermost position. The selection valve 14 in its position connecting the main lead 15 to the lead 17 which is connected to the container 7 containing the matrix beads carrying the living cells.

Figure 2:
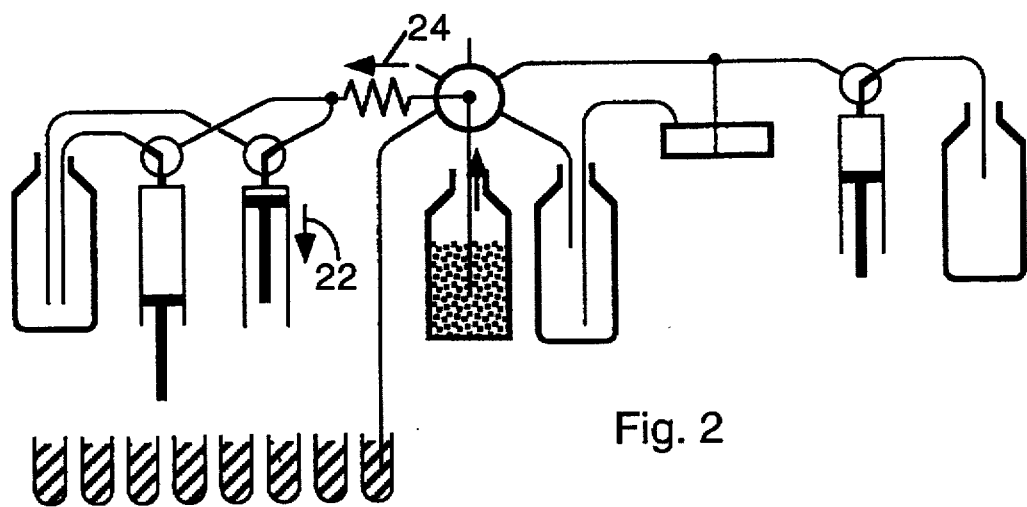

By the second step illustrated in FIG. 2 the piston of the syringe 9 is drawn outwards, as illustrated by the arrow 22 in FIG. 2, and the valve at the outlet of this syringe 9 is in a position connecting this syringe to the main lead 15 of the selection valve 14. Thereby the suction provided by the syringe 9 will cause a suction of matrix beads from the container 7 through the selection valve 14 and into the main lead 15, as illustrated by the arrow 24. A tube coil 21 between the valve 12 and the main lead 15 acts as a reservoir which can absorb a sufficient amount of liquid to avoid that beads are sucked into the syringe 9 or the valve 12.

Figure 3:
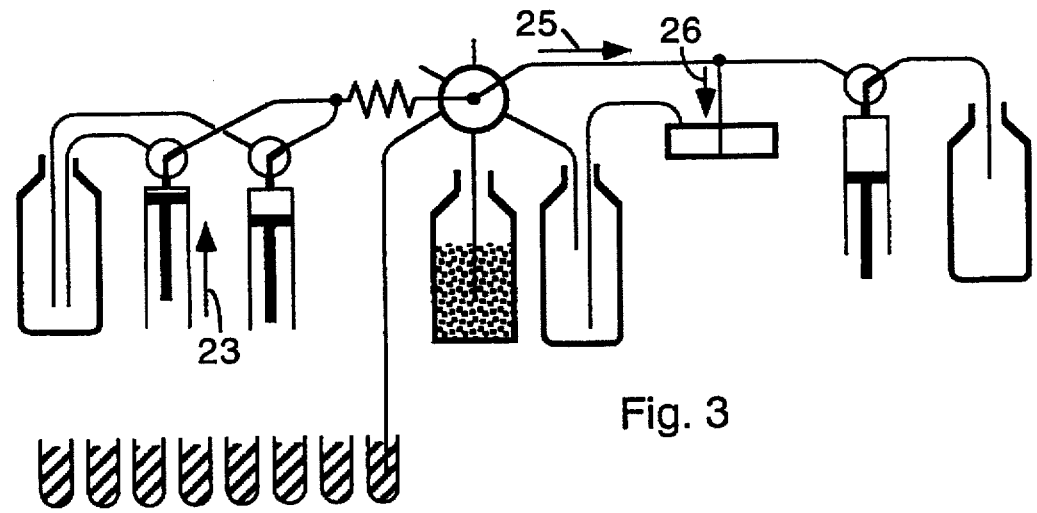

By the third step the piston of the syringe 8 is pressed inward, as illustrated by the arrow 23 in FIG. 3, and the valve 11 at the outlet of this syringe 8 is changed to the position connecting this syringe 8 to the main lead 15 of the selection valve 14 which valve itself connects its main lead 15 to the lead 19 leading to the flow chamber 1. When the piston is pressed into the syringe 8 its content of buffer liquid is pressed into the coil 21 where it displaces the liquid with suspended matrix beads. This matrix bead carrying liquid is led through the lead 19 to the flow chamber 1 as illustrated by the arrows 25 and 26. In the flow chamber 1 the matrix beads are trapped as it will be described below and the buffer liquid carrying the beads flows past and into the waste container 5. At the end of this step the syringe 8 is refilled with buffer from the container 4 before proceeding to the fourth step.

Figure 4:
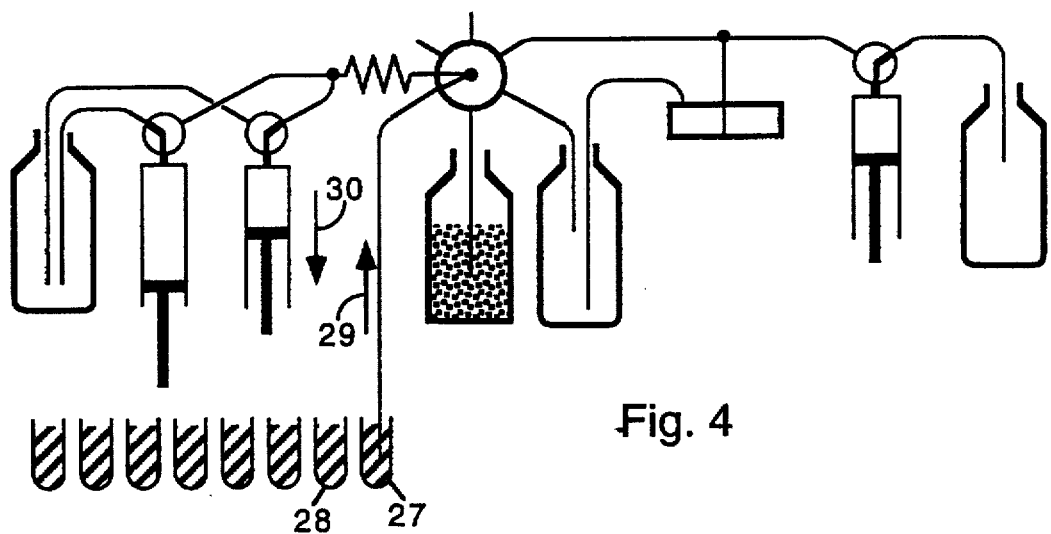
Figure 5:
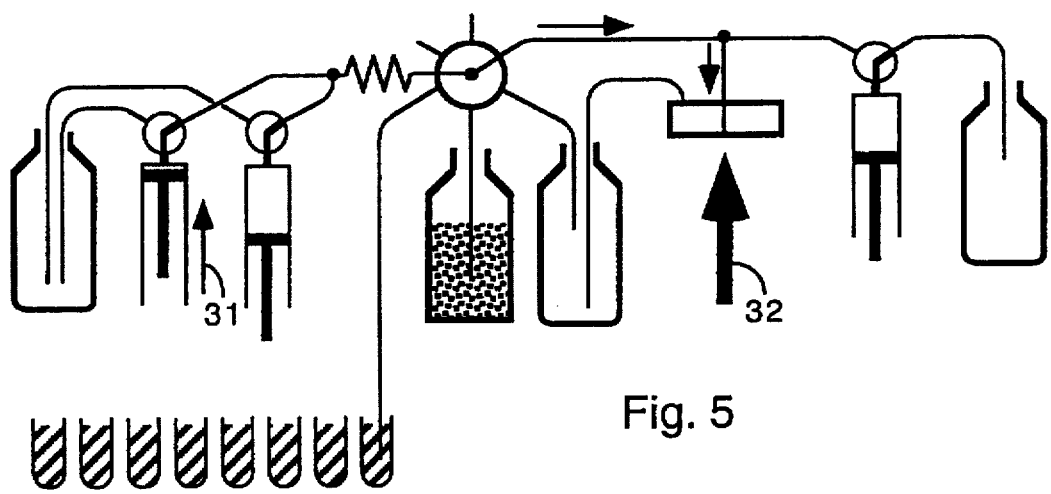

During the fourth step as shown in FIG. 4 the piston of the syringe 8 is drawn out and the selection valve provides a connection to the lead 16 which is inserted into a sample 27 which shall be tested. Therefore, when the piston of the syringe 9 is drawn outward, the sample is sucked into the coil 21 as illustrated by the arrows 29 and 30, and by the fifth step shown in FIG. 5 the sample is propelled to the flow chamber 1 by pressing in the piston of syringe 8 as shown by an arrow 31. During this step the selection valve connects the main lead 15 with the lead 19 leading to the flow chamber 1. The sample washes over the matrix beads trapped in the flow chamber 1 and during this fifth step the signal from the cells on the matrix trapped in the flow chamber 1 is monitored through the wall 2 of the flow chamber 1 by a detector connected to a fluorescence microscope illustrated by a large arrow 32. At the end of the fifth step the syringe 8 is again filled with buffer liquid from the container 4.

Figure 6:
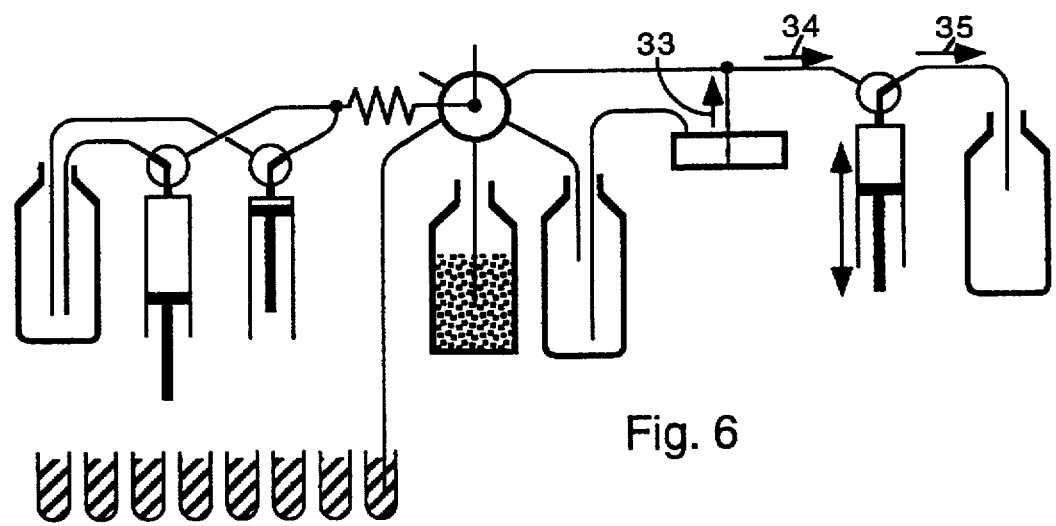

FIG. 6 illustrates the sixth and last step of the process during which step the selection valve is moved to make connection to the lead 20 which may be connected to a waste container not shown. The piston of syringe 10 is moved rapidly outward, aspirating liquid from the waste container 5 through the flow chamber in the reverse direction and into the syringe 10 as illustrated by the arrows 33 and 34. During this aspiration the valve 13 is in the opposite position of the position shown in FIG. 6. At the end of the aspiration stroke the valve 13 is turned to the position shown in FIG. 6 and the piston of the syringe 10 is moved inward to dispense the content of the syringe 10 into the waste container 6 as shown by the arrow 35. Additionally the syringe 9 is emptied through the selector valve 14 into the not shown waste container connected to the lead 20.

Hereafter the system is ready for the next cycle.

During the next cycle the row of samples is conveyed one step forward so that not the sample 27 but the sample 28 is conducted into the flow chamber and so on until a sufficient number of cycles have been performed to test all the samples in the row. As it is seen the whole detecting process may be carried out automatically.

The described embodiment has been shown only for the purpose of illustration and the steps and the number and kind of valves and syringes may be varied and modified widely without deviating from the scope of the invention. Also, the construction of the flow chamber may be varied from that which is described below.

Figure 7:
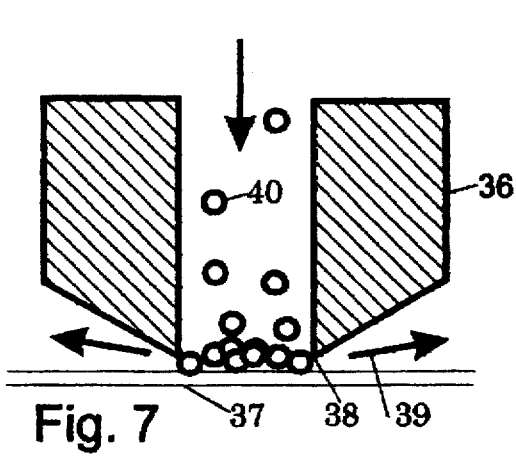
FIG. 7 shows schematically a sectional view of the flow chamber during the fixation of the matrix at an optical surface of an end wall of the chamber.
Figure 8:
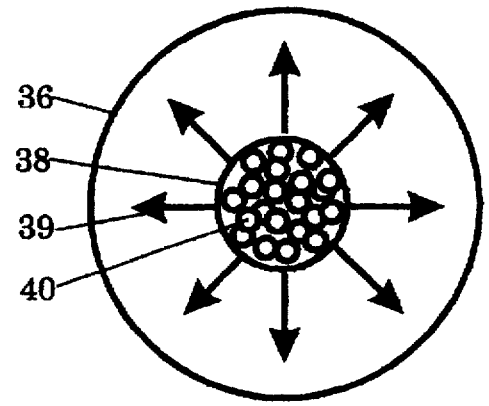
FIG. 8 shows the chamber according to FIG. 7 seen through the end wall of the chamber.

FIG. 7 shows schematically a sectional view of a flow chamber during the filling with matrix carrying beads as described in step three. The flow chamber comprises a ring shaped wall 36 adjacent to a plane optical wall 37. The position of the ring shaped wall 36 relative to the optical wall 37 leaves a gap between an edge 38 of the ring shaped wall and the optical wall which gap is just small enough to keep the matrix beads 40 or droplets trapped in the chamber whereas the liquid may pass through the gap to be led away to a waste container when a liquid with suspended beads or droplets are discharged into the chamber. The escaping liquid is symbolized by the arrows 39. FIG. 8 shows the chamber according to FIG. 7 seen through the optical wall 37.

Figure 9:
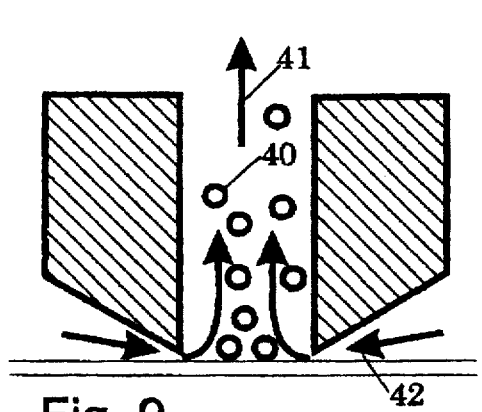
FIG. 9 shows schematically a sectional view of the flow chamber during flushing.
Figure 10:
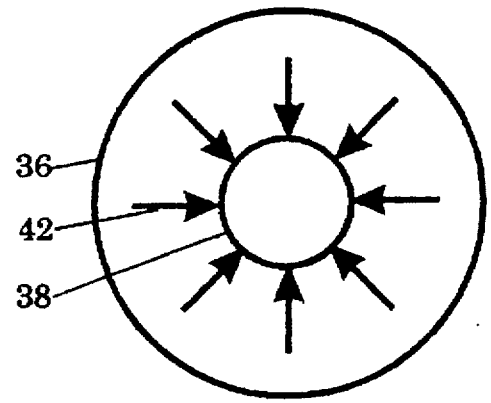
FIG. 10 shows the chamber according to FIG. 9 seen through the end wall of the chamber.
Figure 11:
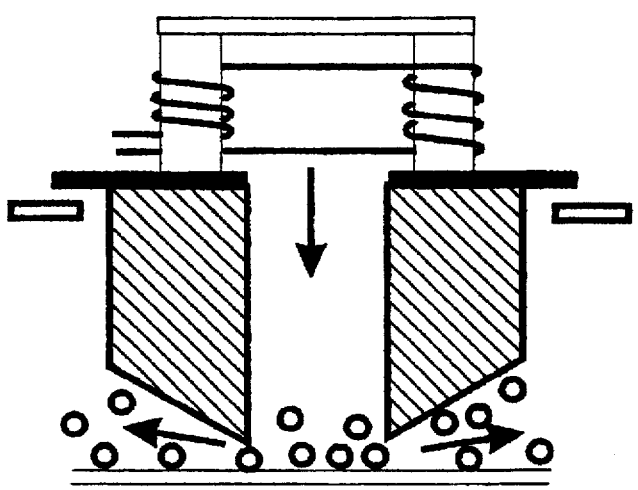
FIG. 11 shows schematically a sectional view of the flow chamber in combination with an electromagnetic means.
Figure 12:
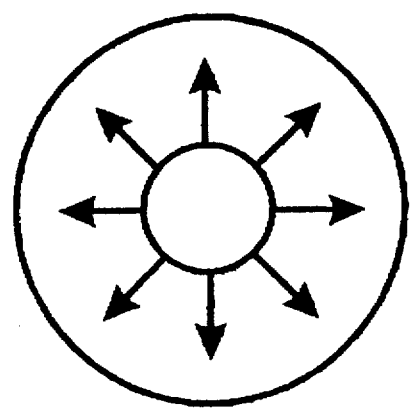
FIG. 12 shows the chamber according to FIG. 11 seen through the end wall of the chamber.

FIG. 9 shows schematically a flow chamber as the one shown in FIGS. 7 and 8 only during the emptying of the chamber as described in the sixth step of the process. Here the liquid is sucked up through the flow chamber as symbolized by the arrows 41 and 42. FIG. 10 shows the chamber of FIG. 9 seen through the wall 37.

As mentioned the components of the apparatus may be modified widely. In an embodiment the ring shaped wall 36 is movable in relation to the optical wall 37. This allows unidirectional flow of liquid through the chamber. During the step by which the flow chamber is filled with the matrix beads or droplets the edge 38 is maintained so close to the optical wall 37 that the matrix beads or droplets are trapped and only the liquid may escape through the gap. When the matrix beads or droplets are to be discharged from the chamber, the wall 36 and its edge 38 is moved away from the optical wall 37 so far that the width of the gap is larger than the diameter of the beads. Thereby the beads may be flushed out through the gap to a waste container. In this way a more effective and quicker flushing of the chamber may be obtained. The changing of the distance between the edge 38 and the optical wall 37 may be controlled by the computer controlling the course and sequence of the steps.

We claim:

1. A flow chamber for rapid, automated screening of cells cultured with a matrix that can fluidically be controlled, the chamber comprising:

(a) an inlet through which fluids can be transported into the chamber, (b) a bottom wall with a plane optical surface through which the content of the chamber can be monitored, and (c) a ring shaped wall having an edge adjacent to the plane optical surface leaving a gap between the edge and the optical surface, the width of the gap allowing liquid but not matrix to pass, means being provided to control the distance between the edge and the optical surface wherein the matrix is momentarily allowed to pass.

2. A flow changer apparatus according to claim 1, wherein the means for controlling the distance between the edge of the ring shaped wall and the optical surface are electromagnets pulling the ring shaped wall and the optical surface away from each other.

* * * * *